United States Patent [19]

Syrinek

[11] Patent Number: 5,605,606

[45] Date of Patent: Feb. 25, 1997

[54] REMOVAL FOULANTS FROM DISTILLATION TRAIN USING NON-SOLVENT PRECIPITATION

[75] Inventor: Allen R. Syrinek, Richmond, Tex.

[73] Assignee: Nalco/Exxon Energy Chemicals. L.P., Sugarland, Tex.

[21] Appl. No.: 491,825

[22] Filed: Jun. 19, 1995

Related U.S. Application Data

[63] Continuation-in-part of Ser. No. 409,777, Mar. 24, 1995, abandoned, which is a continuation-in-part of Ser. No. 93,405, Jul. 19, 1993, abandoned.

[51] Int. Cl.$^6$ .......................................................... B01D 3/34
[52] U.S. Cl. ........................... 203/8; 203/38; 208/48 AA; 210/728; 210/729; 585/864; 585/867
[58] Field of Search ................................... 203/6, 8, 91, 9, 203/68, 60, 66, 62, 69, 63, 38; 208/48 AA, 48 R; 44/412, 430, 432, 392; 585/3–5, 864, 867; 210/728, 729

[56] References Cited

U.S. PATENT DOCUMENTS

| | | | |
|---|---|---|---|
| 3,324,011 | 6/1967 | Baum et al. . | |
| 3,340,186 | 9/1967 | Weyl | 203/10 |
| 3,393,220 | 7/1968 | Winnick et al. . | |
| 3,436,318 | 4/1969 | Glass . | |
| 3,458,430 | 7/1969 | Henselman et al. | 208/33 |
| 3,462,476 | 8/1969 | O'Donnell et al. . | |
| 3,574,088 | 4/1971 | Bsharah et al. | 208/48 R |
| 3,666,633 | 5/1972 | Essex et al. | 203/95 |
| 3,666,656 | 5/1972 | Stanley | 203/7 |
| 3,668,111 | 6/1972 | Duoracek et al. | 208/48 R |
| 4,116,999 | 9/1978 | Barchas . | |
| 4,134,910 | 1/1979 | Barchas et al. . | |
| 4,692,237 | 9/1987 | Hsu et al. | 208/177 |
| 4,944,847 | 7/1990 | Snow | 203/8 |
| 5,100,531 | 3/1992 | Stephenson et al. | 208/22 |
| 5,120,426 | 6/1992 | Johnston et al. | 208/103 |
| 5,213,678 | 5/1993 | Rondum et al. | 203/8 |
| 5,232,577 | 8/1993 | Fetzer et al. | 208/48 AA |
| 5,240,469 | 8/1993 | Poindexter | 203/8 |

FOREIGN PATENT DOCUMENTS 665635  6/1963  Canada .

OTHER PUBLICATIONS

CA78(12):74574: Deparaffination of oils. CA 80 (18):96730p: Saponification of Polyoirel of CA 87(18):138503 u: Improving Fluidity of Petroleum Based Fuel Oils.
CA91(4):21441 p Poly (Lexamethyl–eneimines).

*Primary Examiner*—Virginia Manoharan
*Attorney, Agent, or Firm*—James J. Drake; Robert A. Miller; Patricia A. Charlier

[57] ABSTRACT

A method for the prevention of fouling in a distillation train of a hydrocarbon processing unit. The method involves the precipitation of foulants contained in the hydrocarbon fluid prior to distillation. Precipitation of fouling components occurs when the liquid to be distilled is contacted with a high boiling fluid which is a non-solvent for the foulant causing species but is a solvent for the liquid that is to be distilled.

3 Claims, No Drawings

REMOVAL FOULANTS FROM DISTILLATION TRAIN USING NON-SOLVENT PRECIPITATION

REFERENCE TO RELATED PATENT

The present application is a continuation-in-part of application Ser. No. 08/409,777, now abandoned filed Mar. 24, 1995, by Allen R. Syrinek, entitled "Removal of Foulants from Distillation Train Using Non-Solvent Precipitation," which in turn is a continuation in part of application Ser. No. 08/093,405, now abandoned, filed Jul. 19, 1993 by Allen R. Syrinek entitled "Removal of Foulants from Distillation Train Using Non-Solvent Precipitation", the disclosures of which are incorporated herein by reference.

BACKGROUND OF THE INVENTION

1. Field of the Invention

The invention relates to a method for removal of unwanted foulants from monomers, during monomer preparation, and purification.

2. Description of the Prior Art

Much work has been conducted on the development of additives which may be added to the distillation trains of hydrocarbon processing units to prevent fouling. "Fouling" is often the result of dimer, trimer and polymer formation of the hydrocarbon being distilled. Materials added to prevent fouling have generally been materials that can be categorized as anti-foulants or polymerization inhibitors. Many of these anti-foulants and polymerization inhibitors carry over in the distillation process and great care must be taken to ensure that final product does not contain residual quantities of these materials since they may interfere with the distillates ultimate use.

It would accordingly be a benefit to the art of distillation of reactive hydrocarbons if a method could be found which would eliminate or minimize the use of chemical anti-foulants and polymerization inhibitors. The subject invention which is related to the use of non-solvent precipitating agents provides such a benefit.

Non-solvent precipitation may be defined as the use of a hydrocarbon solvent, or mixtures of hydrocarbon solvents to cause the precipitation of a material to which the non-solvent is mixed while leaving other materials present soluble. This type of technique has been utilized to separate and purify polymers from a system in laboratory scale operations. An example of this technique would be the addition of an aqueous polymer solution of polyacrylamide to a non-solvent of isopropyl alcohol. In this instance, the polymer is precipitated in the alcohol water solution while low molecular weight materials remain solubilized and can be removed.

Non-solvent precipitation may also be utilized in techniques for the determination of molecular weights of polymers, to examine the loss of solvency of crude oil as fractions are removed by distillation. The precipitation of insoluble materials from a non-solvent is a well known phenomenon.

SUMMARY OF THE INVENTION

The subject invention relates to a method for preventing the deposition of fouling components in a distillation train, the distillation train being used to purify an organic fluid containing fouling components, which method comprises the steps of forming a fluid mixture by mixing a first organic fluid with a second fluid. The second fluid is a solvent for the first organic fluid, but it is a non-solvent for fouling components. The formation of a fluid mixture is followed by the steps of precipitating the fouling components from the fluid mixture, separating the fouling components from the fluid mixture and distilling the first organic fluid from the fluid mixture to recover a purified first organic fluid, and reuse of the second high boiling non-solvent, whereby fouling of the distillation train is reduced.

DESCRIPTION OF THE PREFERRED EMBODIMENTS

The subject invention relates to a method for preventing the deposition of fouling components in a distillation train, the distillation train being used to purify an organic fluid containing fouling components, which method comprises the steps of forming a fluid mixture by mixing a first organic fluid with a second fluid.

The first organic fluids to be distilled in this invention include organic liquids which are reactive with themselves and which may form undesirable dimer, trimer and polymeric material fouling components. Typically, materials of this type include vinylic monomers, or monomers which are utilized in condensation polymerization reactions. Examples of vinylic monomers which may be the subject of this invention include but are not limited to known water-soluble vinyl monomers such as acrylamide, acrylic acid, methacrylic add, n-vinyl pyrolidone, acrylamido-methyl propane sulfonic acid, vinyl acetate, vinyl amine, vinyl ethers and the like.

Examples of water-insoluble vinyl monomers which may be the subject of this invention include but are not limited to styrene, vinyl chloride, acrylonitrile, and the like. Examples of monomers used in condensation reactions include $C_2$–$C_8$ dichlorides, diacids, and diamines. Examples of these materials include ethylene dichloride, propylene dichloride, hexamethylene diamine, sebasic acid and the like. The invention finds particular utility in the distillation of styrene and ethylene dichloride.

The second fluid is a solvent for the first organic fluid, but it is a non-solvent for fouling components. Included among the preferred solvents to be used as a second fluid are n-hexane, carbon tetrachloride, toluene, 2-butanone, benzene, cyclohexanone, chlorobenzane, acetone, tetrahydrofuran and methanol. Formation of a fluid mixture is followed by the steps of precipitating the fouling components from the fluid mixture, separating the fouling components from the fluid mixture and distilling the first organic fluid from the fluid mixture to recover a purified first organic fluid whereby fouling of the distillation train is reduced.

Once the fluid mixture of the first and second fluids is formed, it is followed by the steps of precipitating the fouling components from the fluid mixture, separating the fouling components from the fluid mixture and distilling the first organic fluid from the fluid mixture to recover a purified first organic fluid whereby fouling of the distillation train is reduced. Preferably, the separation step is carried out by means of centrifuging and/or simple filtration of solids from the fluid mixture. The second fluid may then be re-used since it is relatively pure. The foulants having been removed by precipitation and the first solvent being removed by distillation.

The step of distilling the first organic fluid from the fluid mixture to recover a purified first organic fluid whereby fouling of the distillation train is reduced depends greatly on the difference in boiling points between the first and second fluids. Table 1 shows a comparison between boiling points of typical first and second fluid combinations. By exploiting this difference, the two fluids can be separated from one another, leaving the relatively pure fluid and away from the first fluid so that it can be re-used in the process.

This invention relates to an improved process of the type disclosed in U.S. Pat. No. 5,045,156, issued to Poindexter, wherein a crude(isophthalonitrile)IPN is fed to a distillation column and a portion of the IPN being distilled is used to solubilize solid impurities formed during the distillation process and which impurities are removed from the distillation column for disposal. Poindexter chooses a solvent for the foulant in the IPN process. This invention chooses a non-solvent for the foulant so that the foulant can be removed from the stream and then reclaim the first solvent by distillation. This leaves relatively pure non-solvent to be re-used in the process.

Fouling of the distillation train is reduced since the foulant must be removed prior to distillation. Preferably, the separation step is carried out by means of centrifugation and/or simple filtration of solids from the fluid mixture.

The step of distilling the first organic fluid from the fluid mixture to recover a purified first organic fluid whereby fouling of the distillation train is reduced depends greatly on the difference in boiling points of typical first and second fluid combinations. By exploiting this difference, the two fluids can be separated from one another. It is preferred to utilize second fluids having boiling points differing from that of the first fluid by at least 20° C. and preferably, at least 40° C. Most preferably the boiling point differential should be at least 100° C. Additionally, the first and second fluids should not form an azeotropic mixture.

The boiling point of the aromatic free hydrocarbon liquids which comprise the first fluid may range from 570° to 750° F. The preferred hydrocarbon liquid first fluids will have boiling points which range between 580° to 700° F.

Exemplary second fluids include, but are not limited to, nonpolar paraffinic hydrocarbon oils, such as pale oils and lubricating oil base stocks. An especially preferred second fluid is Coastal Pale Oil 1200 which is described by its manufacturer, Coastal Petroleum Company, as a lubricating oil base stock. This material may be described by its boiling range which is set forth in Table 1 herein.

TABLE 1

| OBSERVATION | EXTRAPOLATED @ 1 MM HG | @ 5 MM HG | CORRECTED TO 60 MM HG |
| --- | --- | --- | --- |
| Initial Boiling Point | 282 | 340 | 632 |
| 5% Recovered | 375 | 434 | 745 |
| 10% Recovered | 415 | 481 | 800 |
| 20% Recovered | 452 | 518 | 843 |
| 30% Rerovered | 474 | 540 | 868 |
| 40% Recovered | 482 | 551 | 880 |
| 50% Recovered | 501 | 568 | 901 |
| 60% Recovered | 515 | 582 | 917 |
| 70% Recovered | 522 | 593 | 929 |
| 80% Recovered | 540 | 610 | 948 |
| 90% Recovered | 568 | 638 | 980 |
| 95% Recovered | 590 | 662 | 1007 |
| END POINT | 618 | 691 | 1038 |
| RECOVERY | | | 98.0% |
| RESIDUE | | | 2.0% |

* All temperatures are in degrees Fahrenheit; distillation was run at 5 mm Hg[5].

EXAMPLES

In order to exemplify the performance of this invention, the following examples are presented:

A sample of a crude ethylene dichloride was obtained from a manufacturer of ethylene dichloride. This material was black in color and contained approximately 0.0688 grams of solid material per 25 milliliters of volume. This material was used in the examples below.

EXAMPLE I

To a 100 milliliter glass bottle was added, 25 milliliters of the crude ethylene dichloride described above and 25 milliliters of Coastal Pale Oil 1200, a high-boiling saturated hydrocarbon. The mixture was shaken and allowed to settle. The ethylene dichloride/pale oil mixture was observed to be a dark solution containing an estimated 3 volume percent precipitate. This experiment was repeated with 25 milliliters of the crude ethylene dichloride and 50 milliliters of the pale oil. After being allowed to settle an almost clear solution resulted. The precipitate formed was estimated to be approximately 7 volume percent.

EXAMPLE II

A similar experiment was repeated using 1 volume of hexane to 1 volume of the crude ethylene dichloride solution. After mixing and settling, the solution was observed to be dark but not black and the precipitate formed was estimated to be approximately 3 volume percent.

Based upon the above, it is clear that the second fluids selected acted as a precipitant for fouling materials present in the ethylene dichloride first fluid. The first and second fluid mixture so treated may then be distilled using conventional means. Such distillation would result an improved distillation efficiency with less fouling of the distillation efficiency with less fouling of the distillation train compared to the distillation of crude ethylene dichloride not so treated. After distillation of the first fluid from the second fluid, the second fluid may be recombined with additional first fluid and the process repeated.

Changes can be made in the composition, operation and arrangement of the method of the present invention described herein without departing from the concept and scope of the invention as defined in the following claims:

I claim:

1. A method for the reduction of fouling in a distillation train, the distillation train being used to purify an organic fluid containing fouling components which method comprises the steps of:

a. forming a fluid mixture of a first fluid comprising monomers used in condensation polymerization reactions selected from the group consisting of $C_2$–$C_8$ dichlorides, diacids and diamines to be distilled with a second fluid which is a solvent of the first fluid and in which fouling components present in the first fluid are insoluble, the second fluid having a boiling point at least 20° F. greater than the boiling point of the first fluid;

b. precipitating fouling components from the fluid mixture;

c. removing the fluid mixture from the precipitated fouling components;

d. distilling the first fluid from the fluid mixture to recover a purified first fluid whereby fouling of the distillation column is reduced; and e. reusing the second fluid to repeat steps a–d.

2. The method of claim 1 wherein the fouling components are removed from the fluid mixture by a method selected from the group consisting of centrifugal force, filtration and sedimentation.

3. The method of claim 1 wherein the second fluid is selected from the group consisting of n-hexane, carbon tetrachloride, toluene, 2-butanone, benzene, cyclohexanone, chlorobenzene, acetone, tetrahydrofuran and methanol.

* * * * *